(12) United States Patent
Godie

(10) Patent No.: US 6,351,667 B1
(45) Date of Patent: Feb. 26, 2002

(54) DEVICE FOR DETECTING PERICARDIAL EFFUSION

(75) Inventor: Oliver Godie, Stetten (DE)

(73) Assignee: Pulsion Medical Systems AG, Munich (DE)

( * ) Notice: Subject to any disclaimer, the term of this patent is extended or adjusted under 35 U.S.C. 154(b) by 0 days.

(21) Appl. No.: 09/529,840

(22) PCT Filed: Oct. 13, 2000

(86) PCT No.: PCT/EP98/06483

§ 371 Date: Jul. 31, 2000

§ 102(e) Date: Jul. 31, 2000

(87) PCT Pub. No.: WO99/21475

PCT Pub. Date: May 6, 1999

(30) Foreign Application Priority Data

Oct. 24, 1997 (DE) .......................................... 197 47 172

(51) Int. Cl.[7] .................................................. A61B 5/05
(52) U.S. Cl. ........................................ 600/547; 600/481
(58) Field of Search .............................. 600/481, 547, 600/508; 607/17, 24

(56) References Cited

U.S. PATENT DOCUMENTS

| | | | |
|---|---|---|---|
| 3,245,068 A | | 4/1966 | Wegryn et al. |
| 3,971,365 A | | 7/1976 | Smith |
| 4,583,546 A | | 4/1986 | Garde |
| 4,862,361 A | | 8/1989 | Gordon et al. |
| 4,919,136 A | * | 4/1990 | Alt .............................. 607/20 |
| 5,246,008 A | | 9/1993 | Mueller |
| 5,454,377 A | * | 10/1995 | Dzwonczyk et al. ......... 600/547 |
| 5,788,643 A | * | 8/1998 | Feldman ..................... 600/506 |
| 5,800,467 A | * | 9/1998 | Park et al. .................... 607/17 |
| 5,876,353 A | * | 3/1999 | Riff ............................. 600/547 |
| 5,879,308 A | * | 3/1999 | Rasanen ..................... 600/536 |
| 5,978,710 A | * | 11/1999 | Prutchi et al. ................ 607/17 |

FOREIGN PATENT DOCUMENTS

| | | |
|---|---|---|
| EP | 0 487 429 | 5/1992 |
| GB | 2 213 381 | 8/1989 |

* cited by examiner

Primary Examiner—Eric F. Winakur
Assistant Examiner—Charles Marmor, II
(74) Attorney, Agent, or Firm—Squire, Sanders & Dempsey LLP; David B. Abel

(57) ABSTRACT

An apparatus for detecting pericardial effusion that includes a measurement apparatus connected to a wire probe to be anchored on the right heart ventricle and to two other wire probes to be anchored in different regions of the pericardial sac, the measurement apparatus measures and displays the change in impedance between the individual wire probes.

14 Claims, 1 Drawing Sheet

DEVICE FOR DETECTING PERICARDIAL EFFUSION

BACKGROUND OF THE INVENTION

1. Field of the Invention

Figure 1:
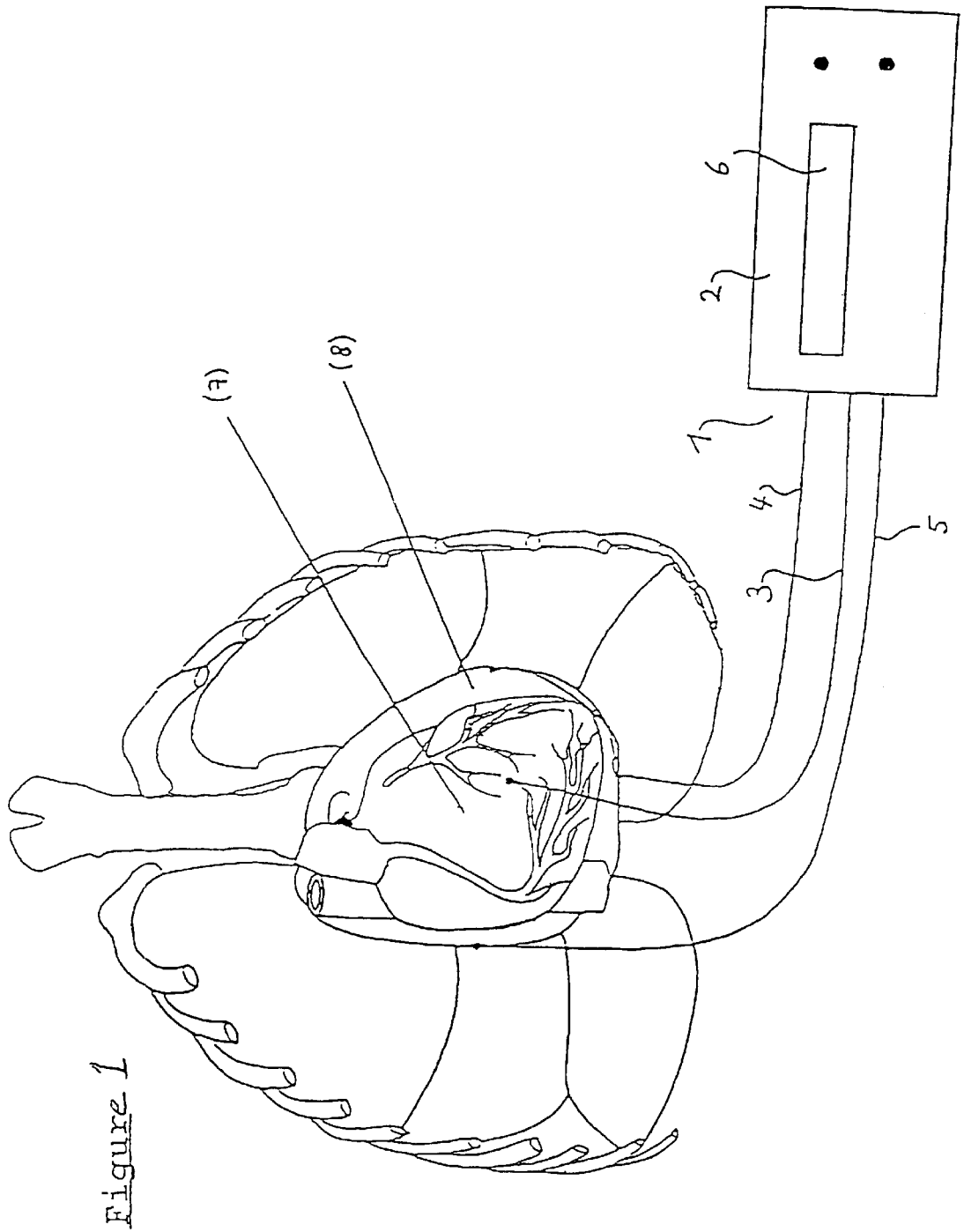

The invention relates to a device for detecting pericardial effusion following heart surgery.

2. Description of the Background Art

In almost every operation performed on the heart, heart valve replacement, bypass surgery, transplantation or fitting of a vascular prosthesis, the pericardium must be opened. Before doing so, it is necessary to cut through the skin, the subcutaneous fatty tissue and the sternum. The operation proper begins once the pericardium has been opened. First, the heart-lung machine is connected up in the same way in all operations. To do this, catheters with large lumina are introduced into the aorta, into the right atrium or the superior and inferior vena cava and into the right pulmonary vein, and the blood is circulated through these catheters once they have been connected up. The patient is cooled to a temperature of between 18° C. and 32° C. and the operation is then performed. In bypass surgery, the coronary vessels are dissected and connected to the bypasses; in heart valve replacement, the aorta and the right or left atrium are opened; in transplantation, all the major vessels leading to or from the heart are cut through and connected to the new heart. After the operation, the patient is warmed up again on the heart-lung machine and is then disconnected from the latter once the cardiovascular conditions have stabilized sufficiently. After inserting a number of drains to lead off the post-operative bleeding, the sternum is closed using wires and the skin is closed with sutures.

As will be evident from the described sequence of a heart operation, very large wound areas are created. If the patient has previously undergone heart surgery, cutting through existing areas of adhesion results in even larger wound areas.

In addition to these wound areas, from which hemorrhaging is possible, there is the further problem of anti-coagulation. To ensure that the blood does not coagulate in the heart-lung machine or in the tubes, medication is first used to render the patient's blood incapable of coagulating. After the operation, medication is once again used to reverse this incoagulability, but this is not always entirely possible. The coagulability of the blood after heart surgery is also limited by the cooling of the body temperature and the contact with the foreign tissue of the heart-lung machine. Thus, after heart surgery, one is faced with the problem of very large wound areas and limited coagulability of the blood. This explains the post-operative bleeding which occurs in these interventions and which can amount to as much as 2000 ml in the first 24 hours after the operation. Replacing the lost blood with blood substitutes can further dilute the blood and thus dispose to hemorrhaging.

To channel off this blood, which gathers mainly in the pericardial sac, the aforementioned drains are inserted. If these drains become blocked, or if they come to lie in such a way that not all the blood can run off, this blood accumulates in the pericardium. If bleeding continues, this compresses the heart, because the pericardium cannot stretch. The result of this compression is that the heart can no longer fill properly and thus cannot pump sufficient blood through the body. This then results in a drop in blood pressure, an increase in central venous pressure, reduced elimination of urine and circulatory centralization. Radiography reveals a widening of the cardiac shadow. This situation is referred to as pericardial tamponade. It is a serious life-threatening situation for the patient; if follow-up surgery is not performed immediately to relieve the pericardium by removing the accumulated blood, this complication will have a fatal outcome.

Pericardial tamponade can only ever be diagnosed on the basis of its clinical picture. Radiography of the thoracic cage showing widening of the cardiac shadow is by itself not sufficient to permit diagnosis. An ultrasound examination is not always reliable since, after an operation, the tissue to be examined is often poorly visualized. In addition to this, both radiography and ultrasound examinations are only carried out when a concrete suspicion exists. This suspicion in most cases arises only when the abovementioned symptoms manifest themselves. However, prior to this suspicion arising, and during the required examinations, valuable time for the patient can be lost.

In the meantime the patient can deteriorate to such an extent that the operation has to be performed under emergency conditions. A delay in performing surgery or even emergency surgery of a pericardial tamponade can again have fatal consequences for the patient as a result of damage to other organ systems, such as the liver and kidneys, or possible infections, or it may considerably prolong the time the patient has to remain in intensive care.

SUMMARY OF THE INVENTION

The object of the invention therefore is to make available a device with which it is possible to continuously monitor the patient for a developing pericardial tamponade and to alert the physician or the nursing staff before the clinical symptoms occur.

This object is achieved by a device for detecting pericardial effusion, which includes a measurement apparatus connected to a wire probe to be anchored on the right heart ventricle and to at least one further wire probe to be anchored in a region of the pericardium, the measurement apparatus measuring and displaying the impedance between the wire probes and comparing the measured impedance values with a zero value or initial value and displaying the change in impedance.

Impedance measurements for recording tissue characteristics or oedemas are known in medicine. Thus, for example, U.S. Pat. No. 5,454,377 describes a method for recording the impedance in the myocardium. Current pulses are generated by means of two electrodes which are anchored in a part of the myocardium, which current pulses generate a voltage between the electrodes. [lacuna] By an impedance spectrum which is characteristic of the myocardial state.

BRIEF DESCRIPTION OF THE ATTACHED DRAWINGS

The device according to the invention is described below with reference to a figure.

FIG. 1 shows a preferred embodiment of the device according to the invention for detecting pericardial effusion in connection with the human heart.

DETAILED DESCRIPTION OF PREFERRED EMBODIMENTS

According to FIG. 1, the device 1 according to the invention includes a measurement apparatus 2 which is connected to a total of three wire probes 3, 4 and 5. The first wire probe 3 can be a conventional temporary pacemaker probe which, in almost every heart operation, is sewn onto the right ventricle 7 before closure of the sternum and is led outside through the skin below the sternum. The pacemaker probe is generally used, in the slow rhythm disturbances often seen after heart operations, to stimulate the heart with the aid of this probe and an external pacemaker and to set the desired heart rate. The wire probe 3 has a diameter of about 0.5 mm and has two poles.

The further probes 4 and 5 connected to the measurement apparatus 2 are to be anchored in the pericardial sac 8. They can be sewn into the pericardial sac to the left and to the right of the heart.

After the probes 3 to 5 have been fixed in the corresponding tissues, it is possible, with the aid of the device according to the invention, to diagnose effusion on the basis of an impedance measurement between the different probes. If, when using the device according to the invention, there is pericardial effusion, the blood or serum which has flown in changes the resistance (impedance) between the probes. The change in impedance between the individual measurement points is measured by the measurement apparatus 2 and shown in a display 6. Since it is possible to measure directly between ventricle and pericardial probes, and also between the pericardial probes, both the extent and position of the effusion can be determined. A precondition for this is a zero value or initial value at which there is no effusion. This initial value can easily be measured before closure of the thoracic cage since at this point the pericardium is suctioned empty with the aid of a suction device. The measurement apparatus 2 then carries out comparisons with the value determined directly thereafter. If the difference exceeds a certain threshold value, the measurement apparatus 2 emits a warning, and, if a further threshold is exceeded, an alarm sounds.

The respective threshold values must be tested correspondingly and determined by trial. If these are taken from a suitably large patient population, the device can be used on any patient without laborious calibration. As has already been mentioned, a single intra-operative zero measurement is necessary.

Exactly in the same way as a pacemaker probe, the necessary probes 3, 4 and 5 can be drawn through the skin and removed after use.

The device 1 must be able to be used safely along with high-frequency current (electric knife) and also during pacemaker mode; it should also have no effect on the pacemaker. Moreover, it should be as small and as light as possible, so that the patient also remains mobile with it. As a result of the light weight of the electronic components of the impedance measurement apparatus 2 and of the probes 3, 4 and 5 used, the device according to the invention can be produced in a manageable size and with low weight as a device that can be easily carried around by a physician or the patient.

Since the device is designed as a routine apparatus, the parts used can be suitable disposable products, as is the case for example with the previously used pacemaker probes.

The device according to the invention affords the postoperative heart patient greater security since the development of pericardial effusion with life-threatening tamponade is continuously monitored and can be detected directly. The extent of an effusion can be directly measured. When the effusion has reached a certain extent, an alarm is triggered and a continuous diagnosis by means of echocardiography or other methods can be initiated without any further delay. The introduction of the probes is uncomplicated and can be done easily by an experienced heart surgeon.

What is claimed is:

1. A device for detecting pericardial effusion, comprising:

a measurement apparatus;

a first wire probe connected to said measurement apparatus, said wire probe being adapted to be anchored on a right heart ventricle; and a second wire probe connected to said measurement apparatus, said second wire probe being adapted to be anchored in a region of a pericardium, wherein said measurement apparatus measures an impedance between said first and second wire probes and compares the measured impedance with a zero value or an initial value and displays a change in impedance.

2. The device of claim 1, further comprising at least one additional wire probe being adapted to be anchored in a different region of the pericardium and connected to said measurement apparatus.

3. The device of claim 1, wherein said measurement apparatus emits an acoustic signal when a defined threshold value for the change in impedance is exceeded.

4. The device of claim 2, further comprising a third wire probe being adapted to be anchored in the pericardium and connected to said measurement apparatus.

5. The device of claim 4, further comprising a fourth wire probe being adapted to be anchored in the pericardium and connected to said measurement apparatus.

6. The device of claim 1, wherein said device is portable.

7. The device of claim 1, wherein said first wire probe is a conventional temporary pacemaker probe and is capable of being sewn onto the right ventricle.

8. A method of detecting pericardial effusion in a patient comprising:

providing a measurement apparatus, providing at least a first wire probe and a second wire probe, said first wire probe and said second wire probe being connected to said measurement apparatus;

anchoring said first wire probe to the right heart ventricle;

anchoring said second wire probe to the pericardium;

repeatedly measuring an impedance between said first wire probe and said second wire probe; and comparing said impedance measured with a reference impedance value and monitoring changes in the compared impedance.

9. The method of claim 8, further comprising the steps of:

providing a third wire probe connected to said measurement apparatus; and anchoring said third wire probe to a second region of the pericardium.

10. The method of claim 8, further comprising the step of emitting an acoustic signal when a predefined threshold value for said compared impedance is exceeded.

11. The method of claim 8, wherein said first wire probe is a pacemaker probe attached to the right heart ventricle.

12. A method for monitoring accumulation of liquid in the pericardium of a patient comprising:

providing a measurement device, a ventricle wire probe and multiple pericardial wire probes attached to said measurement device;

attaching said ventricular wire probe onto a region of a right ventricle;

fixing each of said pericardial wire probes to a separate region of said pericardium;

determining a reference impedance value when no liquid has been accumulated within the pericardium;

monitoring the impedances between said ventricle probe and each of said pericardial probes;

determining a difference between said impedance monitored and said reference impedance value; and signaling any significant variation in the differences between the measured impedances and the reference impedance.

13. The method of claim 12, further comprising the step of providing an alarm warning when said difference between said impedance monitored and said reference impedance value exceeds a predetermined value.

14. The method of claim 12, further comprising the step of continuously monitoring an impedance between said pericardial probes.

* * * * *